United States Patent
Yanagawa et al.

(10) Patent No.: US 9,815,750 B2
(45) Date of Patent: *Nov. 14, 2017

(54) CATALYST FOR PRODUCING MONOCYCLIC AROMATIC HYDROCARBONS, AND METHOD FOR PRODUCING MONOCYCLIC AROMATIC HYDROCARBONS

(71) Applicant: JX Nippon Oil & Energy Corporation, Tokyo (JP)

(72) Inventors: Shinichiro Yanagawa, Tokyo (JP); Masahide Kobayashi, Tokyo (JP); Yuko Aoki, Tokyo (JP); Kazuaki Hayasaka, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 391 days.

This patent is subject to a terminal disclaimer.

(21) Appl. No.: 14/466,444

(22) Filed: Aug. 22, 2014

(65) Prior Publication Data

US 2014/0364666 A1 Dec. 11, 2014

Related U.S. Application Data

(62) Division of application No. 13/138,065, filed as application No. PCT/JP2010/002227 on Mar. 26, 2010, now abandoned.

(30) Foreign Application Priority Data

Jul. 29, 2009 (JP) ................................. 2009-176656

(51) Int. Cl.
*C07C 4/06* (2006.01)
*B01J 29/06* (2006.01)
*B01J 29/40* (2006.01)
*B01J 37/28* (2006.01)

(52) U.S. Cl.
CPC ............... *C07C 4/06* (2013.01); *B01J 29/061* (2013.01); *B01J 29/405* (2013.01); *B01J 37/28* (2013.01); *B01J 2229/37* (2013.01); *C07C 2529/06* (2013.01); *C07C 2529/40* (2013.01); *C07C 2529/85* (2013.01); *C07C 2529/87* (2013.01); *C10G 2300/1033* (2013.01); *C10G 2300/1044* (2013.01); *C10G 2300/1048* (2013.01); *C10G 2300/1051* (2013.01); *C10G 2300/1055* (2013.01); *C10G 2300/1059* (2013.01); *C10G 2300/301* (2013.01); *C10G 2400/30* (2013.01)

(58) Field of Classification Search
USPC ........................................................ 585/476
See application file for complete search history.

(56) References Cited

U.S. PATENT DOCUMENTS

| | | | |
|---|---|---|---|
| 4,394,300 | A | 7/1983 | Chu et al. |
| 4,585,545 | A | 4/1986 | Yancey, Jr. et al. |
| 5,770,047 | A | 6/1998 | Salazar et al. |
| 5,898,089 | A | 4/1999 | Drake et al. |
| 6,255,243 | B1 | 7/2001 | Drake et al. |
| 6,617,275 | B1 | 9/2003 | Sharma et al. |
| 2001/0056217 | A1 | 12/2001 | Froment et al. |
| 2007/0293714 | A1 | 12/2007 | Long et al. |
| 2009/0314683 | A1 | 12/2009 | Matsushita |

FOREIGN PATENT DOCUMENTS

| | | |
|---|---|---|
| EP | 2050731 | 4/2009 |
| JP | 60-019726 | 1/1985 |
| JP | 03-002128 | 1/1991 |
| JP | 03-026791 | 2/1991 |
| JP | 03-052993 | 3/1991 |
| JP | 10-60457 | 3/1998 |
| JP | 2001-525725 | 12/2001 |
| JP | 2002-525380 | 8/2002 |
| JP | 2007-190520 | 8/2007 |
| JP | 2007-530266 | 11/2007 |
| KR | 10-2001-0012397 | 2/2001 |
| WO | WO 98/51409 | 11/1998 |
| WO | WO 00/18853 | 4/2000 |
| WO | WO 2007/135769 | 11/2007 |
| WO | 2010/109897 A1 | 9/2010 |
| WO | WO 2011/001572 | 1/2011 |

(Continued)

OTHER PUBLICATIONS

Office Action dated Jul. 18, 2014 issued in Chinese Application No. 201080028411.1 [with English Translation].

(Continued)

*Primary Examiner* — Elizabeth Wood

(74) *Attorney, Agent, or Firm* — Andrews Kurth Kenyon LLP

(57) ABSTRACT

A catalyst for producing monocyclic aromatic hydrocarbons, used for producing monocyclic aromatic hydrocarbons of 6 to 8 carbon number from a feedstock oil having a 10 volume % distillation temperature of at least 140° C. and an end point temperature of not more than 400° C., wherein the catalyst contains a crystalline aluminosilicate, gallium and/or zinc, and phosphorus, the molar ratio between silicon and aluminum (Si/Al ratio) in the crystalline aluminosilicate is not more than 100, the molar ratio between the phosphorus supported on the crystalline aluminosilicate and the aluminum of the crystalline aluminosilicate (P/Al ratio) is not less than 0.01 and not more than 1.0, and the amount of gallium and/or zinc is not more than 1.2% by mass based on the mass of the crystalline aluminosilicate.

16 Claims, No Drawings

(56) References Cited

FOREIGN PATENT DOCUMENTS

WO    2011/090121 A1    7/2011

OTHER PUBLICATIONS

Office Action dated Apr. 30, 2015 issued in Malaysian Application No. PI2011006058.
International Search Report dated Jun. 29, 2010 issued in corresponding PCT Application No. PCT/JP2010/002227.
Chinese Office Action dated May 24, 2013 issued in corresponding Chinese Application No. 201080032470.6 [with English Translation].
European Search Report dated Jul. 23, 2013 issued in corresponding European Application No. 10804025.4.
International Search Report dated Jun. 29, 2011 issued in related PCT Application No. PCT/JP2010/002171 [with English Translation].
Chinese Office Action dated May 20, 2013 issued in related Chinese Application No. 201080028411.1 [with English Translation].
European Search Report dated Jul. 23, 2013 issued in related European Application No. 10793750.0.
Office Action dated Aug. 29, 2013 issued in U.S. Appl. No. 13/138,082.
Office Action dated Dec. 9, 2015 in corresponding Korean Application No. 10-2012-7002908.
Chun Yang, et al., "Boronation and galliation of zeolite β in an alkaline medium", Materials Chemistry and Physics, vol. 63, pp. 55-66(2000).
International Search Report dated Mar. 6, 2012 in a corresponding PCT application No. PCT/JP2011/080417.
European Search Report dated Jul. 21, 2014 in a corresponding EP application No. 11853615.0.

CATALYST FOR PRODUCING MONOCYCLIC AROMATIC HYDROCARBONS, AND METHOD FOR PRODUCING MONOCYCLIC AROMATIC HYDROCARBONS

This application is a divisional application of U.S. application Ser. No. 13/138,065, filed Jun. 28, 2011, which is a national stage application of International Application No. PCT/JP2010/002227, filed Mar. 26, 2010, which claims priority to Japanese Application No. 2009-176656, filed Jul. 29, 2009, each of which is incorporated by reference in its entirety.

TECHNICAL FIELD

The present invention relates to a catalyst for producing monocyclic aromatic hydrocarbons and a method for producing monocyclic aromatic hydrocarbons that are used for producing monocyclic aromatic hydrocarbons from an oil containing a large amount of polycyclic aromatic hydrocarbons.

Priority is claimed on Japanese Patent Application No. 2009-176656, filed Jul. 29, 2009, the content of which is incorporated herein by reference.

BACKGROUND ART

Light cycle oil (hereinafter also referred to as LCO), which is a cracked gas oil produced in a fluid catalytic cracking, contains a large amount of polycyclic aromatic hydrocarbons, and has been used as a gas oil or a heating oil. However, in recent years, investigations have been conducted into the possibilities of obtaining, from LCO, monocyclic aromatic hydrocarbons of 6 to 8 carbon number (such as benzene, toluene, xylene and ethylbenzene), which can be used as high-octane gasoline base stocks or petrochemical feedstocks, and offer significant added value.

For example, Patent Documents 1 to 3 propose methods that use zeolite catalysts to produce monocyclic aromatic hydrocarbons from the polycyclic aromatic hydrocarbons contained in large amounts within LCO and the like.

However, in the production of monocyclic aromatic hydrocarbons of 6 to 8 carbon number using the catalysts disclosed in Patent Documents 1 to 3, the yield of monocyclic aromatic hydrocarbons of 6 to 8 carbon number during the initial stages of reaction were not entirely satisfactory. Further, the steady-state yield of monocyclic aromatic hydrocarbons of 6 to 8 carbon number has also tended to be low.

When monocyclic aromatic hydrocarbons are produced from a heavy feedstock oil containing polycyclic aromatic hydrocarbons, large amounts of carbon matter are deposited on the catalyst, causing a rapid deterioration in the catalytic activity, and therefore a catalyst regeneration process that removes this carbon matter must be performed frequently. Further, in those cases where a circulating fluidized bed is employed, which is a process in which the reaction and catalyst regeneration are repeated in an efficient manner, the temperature for the catalyst regeneration must be set to a higher temperature than the reaction temperature, resulting in a particularly severe temperature environment for the catalyst.

Under these types of severe conditions, if a zeolite catalyst is used as the catalyst, then the catalyst tends to suffer from hydrothermal degradation, causing a reduction in the steady-state yield of the monocyclic aromatic hydrocarbons, and therefore improvements in the hydrothermal stability of the catalyst are required. However, the zeolite catalysts disclosed in Patent Documents 1 to 3 employ no measures to improve the hydrothermal stability, and offer very little practical usability.

Examples of known methods for improving the hydrothermal stability include a method that uses a zeolite having a high Si/Al ratio, a method in which the catalyst is subjected to a preliminary hydrothermal treatment to stabilize the catalyst, such as USY zeolite, a method in which phosphorus is added to a zeolite, a method in which a rare earth metal is added to a zeolite, and a method that involves improving the structure-directing agent used during the synthesis of a zeolite.

Of these methods, the addition of phosphorus not only improves the hydrothermal stability, but also provides other known effects such as an improvement in selectivity due to suppression of carbon matter deposition during fluid catalytic cracking, and an improvement in the abrasion resistance of the binder. Accordingly, this method is frequently applied to catalysts used in catalytic cracking reactions.

Examples of catalytic cracking catalysts prepared by adding phosphorus to a zeolite include those disclosed in Patent Documents 4 to 6.

Namely, Patent Document 4 discloses a method for producing olefins from naphtha using a catalyst containing ZSM-5 to which has been added phosphorus, as well as gallium, germanium and/or tin. In Patent Document 4, phosphorus is added for the purposes of suppressing the production of methane and aromatics in order to enhance the selectivity for olefin production, and ensuring a high degree of activity even for a short contact time, thereby improving the yield of olefins.

Patent Document 5 discloses a method for producing olefins in a high yield from heavy hydrocarbons by using a catalyst prepared by supporting phosphorus on ZSM-5 containing zirconium and a rare earth element, and a catalyst containing a USY zeolite, an REY zeolite, kaolin, silica and alumina.

Patent Document 6 discloses a method for producing ethylene and propylene in a high yield by transforming hydrocarbons using a catalyst containing ZSM-5 having phosphorus and a transition metal element support thereon.

As mentioned above, the addition of phosphorus to zeolites has been disclosed in Patent Documents 4 to 6, but in each of these documents, the main purpose was improvement of the olefin yield, and monocyclic aromatic hydrocarbons of 6 to 8 carbon number were not able to be produced at high yield. For example, Table 2 in Patent Document 6 discloses the yields for olefins (ethylene and propylene) and BTX (benzene, toluene and xylene), and whereas the yield for the olefins was 40% by mass, the yield for BTX was a low value of approximately 6% by mass.

Accordingly, a catalyst for producing monocyclic aromatic hydrocarbons that is capable of producing monocyclic aromatic hydrocarbons of 6 to 8 carbon number in a high yield from a feedstock oil containing polycyclic aromatic hydrocarbons, not only during the initial reaction but also under steady-state conditions, is not currently known.

DOCUMENTS OF RELATED ART

Patent Documents

[Patent Document 1]
Japanese Unexamined Patent Application, First Publication No. Hei 3-2128

[Patent Document 2]
Japanese Unexamined Patent Application, First Publication No. Hei 3-52993
[Patent Document 3]
Japanese Unexamined Patent Application, First Publication No. Hei 3-26791
[Patent Document 4]
Published Japanese Translation No. 2002-525380 of PCT
[Patent Document 5]
Japanese Unexamined Patent Application, First Publication No. 2007-190520
[Patent Document 6]
Published Japanese Translation No. 2007-530266 of PCT

SUMMARY OF INVENTION

Problems to be Solved by the Invention

An object of the present invention is to provide a catalyst for producing monocyclic aromatic hydrocarbons and a method for producing monocyclic aromatic hydrocarbons that are capable of producing monocyclic aromatic hydrocarbons of 6 to 8 carbon number in a high yield from a feedstock oil containing polycyclic aromatic hydrocarbons, not only during the initial reaction but also under steady-state conditions.

Means to Solve the Problems

[1] A catalyst for producing monocyclic aromatic hydrocarbons, used for producing monocyclic aromatic hydrocarbons of 6 to 8 carbon number from a feedstock oil having a 10 volume % distillation temperature of at least 140° C. and an end point temperature of not more than 400° C., wherein
the catalyst contains a crystalline aluminosilicate, gallium and/or zinc, and phosphorus, the molar ratio between silicon and aluminum (Si/Al ratio) in the crystalline aluminosilicate is not more than 100, the molar ratio between the phosphorus supported on the crystalline aluminosilicate and the aluminum of the crystalline aluminosilicate (P/Al ratio) is not less than 0.01 and not more than 1.0, and the amount of gallium and/or zinc is not more than 1.2% by mass based on the mass of the crystalline aluminosilicate.
[2] The catalyst for producing monocyclic aromatic hydrocarbons according to [1], wherein the amount of phosphorus is within a range from 0.1 to 10% by mass based on the total mass of the catalyst, and the amount of gallium and/or zinc contained within the catalyst is not more than 2% by mass based on the total mass of the catalyst.
[3] The catalyst for producing monocyclic aromatic hydrocarbons according to [1] or [2], wherein the crystalline aluminosilicate is a pentasil-type zeolite.
[4] The catalyst for producing monocyclic aromatic hydrocarbons according to any one of [1] to [3], wherein the crystalline aluminosilicate is an MFI-type zeolite.
[5] The catalyst for producing monocyclic aromatic hydrocarbons according to any one of [1] to [4], wherein the molar ratio between the phosphorus supported on the crystalline aluminosilicate and the aluminum of the crystalline aluminosilicate (P/Al ratio) is not more than 0.5.
[6] The catalyst for producing monocyclic aromatic hydrocarbons according to any one of [1] to [5], wherein the amount of gallium and/or zinc is not more than 1.0% by mass based on the mass of the crystalline aluminosilicate.
[7] A method for producing monocyclic aromatic hydrocarbons of 6 to 8 carbon number, the method including bringing a feedstock oil having a 10 volume % distillation temperature of at least 140° C. and an end point temperature of not more than 400° C. into contact with the catalyst for producing monocyclic aromatic hydrocarbons according to any one of [1] to [5].
[8] A method for producing monocyclic aromatic hydrocarbons of 6 to 8 carbon number, the method including bringing a feedstock oil having a 10 volume % distillation temperature of at least 140° C. and a 90 volume % distillation temperature of not more than 350° C. into contact with the catalyst for producing monocyclic aromatic hydrocarbons according to any one of [1] to [5].
[9] The method for producing monocyclic aromatic hydrocarbons of 6 to 8 carbon number according to [7] or [8], wherein a cracked gas oil produced in a fluid catalytic cracking is used as the feedstock oil.
[10] The method for producing monocyclic aromatic hydrocarbons of 6 to 8 carbon number according to any one of [7] to [9], wherein the feedstock oil is brought into contact with the catalyst for producing monocyclic aromatic hydrocarbons in a fluidized bed reactor.

Effect of the Invention

The catalyst for producing monocyclic aromatic hydrocarbons and the method for producing monocyclic aromatic hydrocarbons of 6 to 8 carbon number according to the present invention enable the production of monocyclic aromatic hydrocarbons of 6 to 8 carbon atoms in a high yield from a feedstock oil containing polycyclic aromatic hydrocarbons. Moreover, the yield of monocyclic aromatic hydrocarbons of 6 to 8 carbon number is high even under steady-state conditions.

DESCRIPTION OF EMBODIMENTS

Catalyst for Producing Monocyclic Aromatic Hydrocarbons

The catalyst for producing monocyclic aromatic hydrocarbons according to the present invention (hereinafter often referred to as "the catalyst") is used for producing monocyclic aromatic hydrocarbons of 6 to 8 carbon number (hereinafter often abbreviated as "monocyclic aromatic hydrocarbons") from a feedstock oil containing polycyclic aromatic hydrocarbons, and contains a crystalline aluminosilicate, gallium and/or zinc, and phosphorus.

[Crystalline Aluminosilicate]

Although there are no particular limitations on the crystalline aluminosilicate, medium pore size zeolites such as zeolites with MFI, MEL, TON, MTT, MRE, FER, AEL and EUO type crystal structures are preferred, and in terms of maximizing the yield of monocyclic aromatic hydrocarbons, pentasil-type zeolites are more preferred, and zeolites with MFI-type and/or MEL-type crystal structures are particularly desirable.

MFI-type and MEL-type zeolites are included within the conventional zeolite structures published by The Structure Commission of the International Zeolite Association (Atlas of Zeolite Structure Types, W. M. Meiyer and D. H. Olson (1978), distributed by Polycrystal Book Service, Pittsburgh, Pa. (USA).

The amount of the crystalline aluminosilicate within the catalyst, relative to a value of 100% for the entire catalyst, is preferably within a range from 10 to 95% by mass, more preferably from 20 to 80% by mass, and still more preferably from 25 to 70% by mass. Provided the amount of the crystalline aluminosilicate is not less than 10% by mass and not more than 95% by mass, a satisfactorily high level of catalytic activity can be achieved.

In the crystalline aluminosilicate, the molar ratio between silicon and aluminum (Si/Al ratio) is not more than 100, and is preferably not more than 50. If the Si/Al ratio of the crystalline aluminosilicate exceeds 100, then the yield of monocyclic aromatic hydrocarbons tends to decrease.

Further, in terms of maximizing the yield of monocyclic aromatic hydrocarbons, the Si/Al ratio of the crystalline aluminosilicate is preferably at least 10.

[Gallium]

Examples of the form of the gallium contained within the catalyst of the present invention include catalysts in which the gallium is incorporated within the lattice framework of the crystalline aluminosilicate (crystalline aluminogallosilicates), catalysts in which gallium is supported on the crystalline aluminosilicate (gallium-supporting crystalline aluminosilicates), and catalysts including both of these forms.

A crystalline aluminogallosilicate has a structure in which $SiO_4$, $AlO_4$ and $GaO_4$ structures adopt tetrahedral coordination within the framework. A crystalline aluminogallosilicate can be obtained, for example, by gel crystallization via hydrothermal synthesis, by a method in which gallium is inserted into the lattice framework of a crystalline aluminosilicate, or by a method in which aluminum is inserted into the lattice framework of a crystalline gallosilicate.

A gallium-supporting crystalline aluminosilicate can be obtained by supporting gallium on a crystalline aluminosilicate using a conventional method such as an ion-exchange method or impregnation method. There are no particular limitations on the gallium source used in these methods, and examples include gallium salts such as gallium nitrate and gallium chloride, and gallium oxide.

The amount of gallium within the catalyst of the present invention, relative to a value of 100% for the total mass of the crystalline aluminosilicate, is typically not more than 1.2% by mass, preferably not more than 1.0% by mass, still more preferably not more than 0.8% by mass, and most preferably not more than 0.5% by mass. If the amount of gallium exceeds 1.2% by mass, then the yield of monocyclic aromatic hydrocarbons tends to decrease.

Further, the amount of gallium within the catalyst of the present invention, relative to a value of 100% for the total mass of the crystalline aluminosilicate, is preferably not less than 0.01% by mass, and more preferably 0.1% by mass or greater. If the amount of gallium is less than 0.01% by mass, then the yield of monocyclic aromatic hydrocarbons may decrease.

[Zinc]

Examples of the form of the zinc contained within the catalyst of the present invention include catalysts in which the zinc is incorporated within the lattice framework of the crystalline aluminosilicate (crystalline aluminozincosilicates), catalysts in which zinc is supported on the crystalline aluminosilicate (zinc-supporting crystalline aluminosilicates), and catalysts including both of these forms.

A crystalline aluminozincosilicate has a structure in which $SiO_4$, $AlO_4$ and $ZnO_4$ structures exist within the framework. A crystalline aluminozincosilicate can be obtained, for example, by gel crystallization via hydrothermal synthesis, by a method in which zinc is inserted into the lattice framework of a crystalline aluminosilicate, or by a method in which aluminum is inserted into the lattice framework of a crystalline zincosilicate.

A zinc-supporting crystalline aluminosilicate can be obtained by supporting zinc on a crystalline aluminosilicate using a conventional method such as an ion-exchange method or impregnation method. There are no particular limitations on the zinc source used in these methods, and examples include zinc salts such as zinc nitrate and zinc chloride, and zinc oxide.

The amount of zinc within the catalyst of the present invention, relative to a value of 100% for the total mass of the crystalline aluminosilicate, is typically not more than 1.2% by mass, preferably not more than 1.0% by mass, still more preferably not more than 0.8% by mass, and most preferably not more than 0.7% by mass. If the amount of zinc exceeds 1.2% by mass, then the yield of monocyclic aromatic hydrocarbons tends to decrease.

Further, the amount of zinc, relative to a value of 100% for the total mass of the crystalline aluminosilicate, is preferably not less than 0.01% by mass, and more preferably 0.1% by mass or greater. If the amount of zinc is less than 0.01% by mass, then the yield of monocyclic aromatic hydrocarbons may decrease.

The catalyst of the present invention may be a catalyst that contains either one of gallium or zinc, or a catalyst that contains both gallium and zinc. Further, the catalyst may also contain one or more other metals in addition to the gallium and/or zinc.

[Phosphorus]

The molar ratio between the phosphorus supported on the crystalline aluminosilicate and the aluminum contained within the crystalline aluminosilicate (P/Al ratio) is not more than 1.0, and is preferably 0.5 or less. If the P/Al ratio exceeds 1.0, then the yield of monocyclic aromatic hydrocarbons tends to decrease.

Further, the P/Al ratio is typically at least 0.01. If the P/Al ratio is less than 0.01, then the steady-state yield of monocyclic aromatic hydrocarbons may decrease, which is undesirable.

There are no particular limitations on the method used for incorporating the phosphorus within the catalyst of the present invention, and examples include methods in which an ion-exchange method or impregnation method or the like is used to support phosphorus on a crystalline aluminosilicate, crystalline aluminogallosilicate or crystalline aluminozincosilicate, methods in which a phosphorus compound is added during synthesis of the zeolite, thereby substituting a portion of the internal framework of the crystalline aluminosilicate with phosphorus, and methods in which a crystallization promoter containing phosphorus is used during synthesis of the zeolite. Although there are no particular limitations on the phosphate ion-containing aqueous solution used during the above methods, a solution prepared by dissolving phosphoric acid, diammonium hydrogen phosphate, ammonium dihydrogen phosphate or another water-soluble phosphate salt in water at an arbitrary concentration can be used particularly favorably.

The catalyst of the present invention can be obtained by calcining (at a calcination temperature of 300 to 900° C.) an above-mentioned phosphorus-supporting crystalline aluminogallosilicate or crystalline aluminozincosilicate, or a crystalline aluminosilicate having gallium/zinc and phosphorus supported thereon.

[Form]

The catalyst of the present invention is used in the form of a powder, granules or pellets or the like, depending on the reaction format. For example, a powder is used in the case of a fluidized bed, whereas granules or pellets are used in the case of a fixed bed. The average particle size of the catalyst used in a fluidized bed is preferably within a range from 30 to 180 μm, and more preferably from 50 to 100 μm. Further, the bulk density of the catalyst used in a fluidized bed is preferably within a range from 0.4 to 1.8 g/cc, and more preferably from 0.5 to 1.0 g/cc.

The average particle size describes the particle size at which the particle size distribution obtained by classification using sieves reaches 50% by mass, whereas the bulk density refers to the value measured using the method prescribed in JIS R 9301-2-3.

In order to obtain a catalyst in granular or pellet form, if necessary, an inert oxide may be added to the catalyst as a binder or the like, with the resulting mixture then molded using any of various molding apparatus.

In those cases where the catalyst of the present invention contains an inorganic oxide such as a binder, a compound that contains phosphorus may also be used as the binder.

Further, in those cases where the catalyst contains an inorganic oxide such as a binder, the catalyst may be produced by mixing the binder and the crystalline aluminosilicate, and subsequently adding the gallium and/or zinc and the phosphorus, or by mixing the binder and the gallium- and/or zinc-supporting crystalline aluminosilicate, or mixing the binder and the crystalline aluminogallosilicate and/or crystalline aluminozincosilicate, and subsequently adding the phosphorus.

In those cases where the catalyst contains an inorganic oxide such as a binder, the amount of phosphorus relative to the total mass of the catalyst is preferably within a range from 0.1 to 10% by mass. Further, the lower limit for this range is more preferably at least 0.2% by mass, whereas the upper limit is more preferably not more than 5.0% by mass, and still more preferably not more than 2.0% by mass. By ensuring that the amount of phosphorus is at least 0.1% by mass of the total mass of the catalyst, deterioration over time in the yield of the monocyclic aromatic hydrocarbons can be prevented. On the other hand, ensuring that the amount of phosphorus is not more than 10% by mass means that the yield of the monocyclic aromatic hydrocarbons can be increased.

Further, in those cases where the catalyst contains an inorganic oxide such as a binder, the amount of gallium and/or zinc relative to the total mass of the catalyst is preferably not more than 2% by mass, more preferably not more than 1.5% by mass, and still more preferably not more than 1.2% by mass. If the amount of gallium and/or zinc exceeds 2% by mass based on the total mass of the catalyst, then the yield of monocyclic aromatic hydrocarbons tends to decrease, which is undesirable.

(Method for Producing Monocyclic Aromatic Hydrocarbons)

The method for producing monocyclic aromatic hydrocarbons according to the present invention involves bringing a feedstock oil into contact with the above-mentioned catalyst to effect reaction.

In this reaction, saturated hydrocarbons function as hydrogen donor sources, and a hydrogen transfer reaction from the saturated hydrocarbons is used to convert polycyclic aromatic hydrocarbons into monocyclic aromatic hydrocarbons.

[Feedstock Oil]

The feedstock oil used in the present invention is preferably either an oil having a 10 volume % distillation temperature of at least 140° C. and an end point temperature of not more than 400° C., or an oil having a 10 volume % distillation temperature of at least 140° C. and a 90 volume % distillation temperature of not more than 360° C. With an oil having a 10 volume % distillation temperature of less than 140° C., the reaction involves production of BTX from light compounds, which is outside the scope of the present invention, and therefore the 10 volume % distillation temperature is preferably at least 140° C., and more preferably 150° C. or higher. Further, if an oil having an end point temperature exceeding 400° C. is used, then not only is the yield of monocyclic aromatic hydrocarbons low, but the amount of coke deposition on the catalyst also tends to increase, causing a more rapid deterioration in the catalytic activity, and therefore the end point temperature of the feedstock oil is preferably not more than 400° C., and more preferably 380° C. or lower. Furthermore, if a feedstock oil having a 90 volume % distillation temperature that exceeds 360° C. is used, then the amount of coke deposition on the catalyst tends to increase, causing a more rapid deterioration in the catalytic activity, and therefore the 90 volume % distillation temperature for the feedstock oil is preferably not more than 360° C., and more preferably 350° C. or lower.

In this description, the 10 volume % distillation temperature, the 90 volume % distillation temperature and the end point temperature refer to values measured in accordance with the methods prescribed in JIS K 2254 "Petroleum products—determination of distillation characteristics".

Examples of feedstock oils having a 10 volume % distillation temperature of at least 140° C. and an end point temperature of not more than 400° C., or feedstock oils having a 10 volume % distillation temperature of at least 140° C. and a 90 volume % distillation temperature of not more than 360° C. include cracked gas oil (LCO) produced in a fluid catalytic cracking, coal liquefaction oil, hydrocracked oil from heavy oils, straight-run kerosene, straight-run gas oil, coker kerosene, coker gas oil, and hydrocracked oil from oil sands.

Further, if the feedstock oil contains a very large amount of polycyclic aromatic hydrocarbons, then the yield of monocyclic aromatic hydrocarbons of 6 to 8 carbon number tends to decrease, and therefore the amount of polycyclic aromatic hydrocarbons (the polycyclic aromatic content) within the feedstock oil is preferably not more than 50 volume %, and more preferably 30 volume % or less.

In this description, the polycyclic aromatic content describes the combined total of the amount of bicyclic aromatic hydrocarbons (the bicyclic aromatic content) and the amount of tricyclic and higher aromatic hydrocarbons (the tricyclic and higher aromatic content) measured in accordance with JPI-5S-49 "Petroleum Products—Determination of Hydrocarbon Types—High Performance Liquid Chromatography".

[Reaction Format]

Examples of the reaction format used for bringing the feedstock oil into contact with the catalyst for reaction include fixed beds, moving beds and fluidized beds. In the present invention, because a heavy oil fraction is used as the feedstock, a fluidized bed is preferred as it enables the coke fraction adhered to the catalyst to be removed in a continuous manner and enables the reaction to proceed in a stable manner. A continuous regeneration-type fluidized bed, in which the catalyst is circulated between the reactor and a regenerator, thereby continuously repeating a reaction-regeneration cycle, is particularly desirable. The feedstock oil that makes contact with the catalyst is preferably in a gaseous state. Further, the feedstock may be diluted with a gas if required. Furthermore, in those cases where unreacted feedstock occurs, this may be recycled as required.

[Reaction Temperature]

Although there are no particular limitations on the reaction temperature during contact of the feedstock oil with the catalyst for reaction, a reaction temperature of 350 to 700° C. is preferred. In terms of achieving satisfactory reactivity, the lower limit is more preferably 450° C. or higher. On the other hand, an upper limit temperature of not more than 650° C. is preferable, as it is not only more advantageous from an energy perspective, but also enables ready regeneration of the catalyst.

[Reaction Pressure]

The reaction pressure during contact of the feedstock oil with the catalyst for reaction is preferably not more than 1.0 MPaG. Provided the reaction pressure is not more than 1.0 MPaG, the generation of by-product light gases can be prevented, and the pressure resistance required for the reaction apparatus can be lowered.

[Contact Time]

There are no particular limitations on the contact time between the feedstock oil and the catalyst, provided the desired reaction proceeds satisfactorily, but in terms of the gas transit time across the catalyst, a time of 1 to 300 seconds is preferred. The lower limit for this time is more preferably at least 5 seconds, and the upper limit is more preferably 150 seconds or less. Provided the contact time is at least 1 second, a reliable reaction can be achieved, whereas provided the contact time is not more than 300 seconds, deposition of carbon matter on the catalyst due to coking or the like can be suppressed. Further, the amount of light gas generated by cracking can also be suppressed.

In the method for producing monocyclic aromatic hydrocarbons according to the present invention, hydrogen transfer occurs from saturated hydrocarbons to the polycyclic aromatic hydrocarbons, and the polycyclic aromatic hydrocarbons undergo partial hydrogenation and ring opening, yielding monocyclic aromatic hydrocarbons.

In the present invention, the yield of monocyclic aromatic hydrocarbons in the initial reaction is preferably at least 25% by mass, more preferably at least 30% by mass, and still more preferably 35% by mass or greater.

Further, the steady-state yield of monocyclic aromatic hydrocarbons is preferably at least 20% by mass, more preferably at least 25% by mass, and still more preferably 30% by mass or greater.

If the yield of monocyclic aromatic hydrocarbons during the initial reaction is less than 25% by mass, or the steady-state yield of monocyclic aromatic hydrocarbons is less than 20% by mass, then the concentration of monocyclic aromatic hydrocarbons within the reaction product is low, and the efficiency with which those compounds can be recovered tends to deteriorate.

In the above-mentioned production method of the present invention, because the catalyst described above is used, monocyclic aromatic hydrocarbons can be produced in a high yield, both during the initial reaction and under steady-state conditions.

EXAMPLES

The present invention is described in more detail below based on a series of examples and comparative examples, but the present invention is in no way limited by these examples.

Preparation of Catalysts

Catalyst Preparation Example 1

120 g of a proton-type crystalline aluminosilicate having an MFI structure and a silicon/aluminum molar ratio (Si/Al ratio) of 15 was impregnated with 120 g of a 1.15% by mass aqueous solution of gallium nitrate octahydrate in order to support 0.2% by mass of gallium on the aluminosilicate (based on a value of 100% for the total mass of the crystalline aluminosilicate), and the resulting product was then dried at 120° C. Subsequently, the product was calcined for 3 hours at 780° C. under a stream of air, yielding a gallium-supporting crystalline aluminosilicate.

Subsequently, 30 g of the obtained gallium-supporting crystalline aluminosilicate was impregnated with 30 g of a 3.20% by mass aqueous solution of diammonium hydrogen phosphate, and the resulting product was then dried at 120° C. Subsequently, the product was calcined for 3 hours at 780° C. under a stream of air, yielding a catalyst containing the crystalline aluminosilicate, gallium and phosphorus.

Tablet molding was performed by applying a pressure of 39.2 MPa (400 kgf) to the obtained catalyst, and the resulting tablets were subjected to coarse crushing and then classified using a 20 to 28 mesh size, thus yielding a granular catalyst 1 (hereinafter referred to as the "granulated catalyst 1"). The Si/Al ratio within the granulated catalyst 1 was 15, the molar ratio between phosphorus and aluminum (P/Al ratio) was 0.23, and the amount of gallium (based on a value of 100% for the total mass of the crystalline aluminosilicate) was 0.2% by mass.

Catalyst Preparation Example 2

With the exception of preparing a gallium-supporting crystalline aluminosilicate using a proton-type crystalline aluminosilicate having an MFI structure and a silicon/aluminum molar ratio (Si/Al ratio) of 35, and then impregnating 30 g of the thus obtained gallium-supporting crystalline aluminosilicate with 30 g of a 1.40% by mass aqueous solution of diammonium hydrogen phosphate, a granular catalyst 2 (hereinafter referred to as the "granulated catalyst 2") was obtained in the same manner as that described in Catalyst preparation example 1. The Si/Al ratio within the granulated catalyst 2 was 35, the molar ratio between phosphorus and aluminum (P/Al ratio) was 0.23, and the amount of gallium (based on a value of 100% for the total mass of the crystalline aluminosilicate) was 0.2% by mass.

Catalyst Preparation Example 3

With the exception of preparing a gallium-supporting crystalline aluminosilicate using a proton-type crystalline aluminosilicate having an MFI structure and a silicon/aluminum molar ratio (Si/Al ratio) of 50, and then impregnating 30 g of the thus obtained gallium-supporting crystalline aluminosilicate with 30 g of a 1.00% by mass aqueous solution of diammonium hydrogen phosphate, a granular catalyst 3 (hereinafter referred to as the "granulated catalyst 3") was obtained in the same manner as that described in Catalyst preparation example 1. The Si/Al ratio within the granulated catalyst 3 was 50, the molar ratio between phosphorus and aluminum (P/Al ratio) was 0.23, and the amount of gallium (based on a value of 100% for the total mass of the crystalline aluminosilicate) was 0.2% by mass.

Catalyst Preparation Example 4

With the exception of preparing a gallium-supporting crystalline aluminosilicate using a proton-type crystalline aluminosilicate having an MFI structure and a silicon/aluminum molar ratio (Si/Al ratio) of 100, and then impregnating 30 g of the thus obtained gallium-supporting crystalline aluminosilicate with 30 g of a 0.50% by mass aqueous solution of diammonium hydrogen phosphate, a granular catalyst 4 (hereinafter referred to as the "granulated catalyst 4") was obtained in the same manner as that described in Catalyst preparation example 1. The Si/Al ratio within the granulated catalyst 4 was 100, the molar ratio between phosphorus and aluminum (P/Al ratio) was 0.23, and the amount of gallium (based on a value of 100% for the total mass of the crystalline aluminosilicate) was 0.2% by mass.

Catalyst Preparation Example 5

With the exception of preparing a gallium-supporting crystalline aluminosilicate using a proton-type crystalline aluminosilicate having an MFI structure and a silicon/aluminum molar ratio (Si/Al ratio) of 200, and then impregnating 30 g of the thus obtained gallium-supporting crystalline aluminosilicate with 30 g of a 0.27% by mass aqueous solution of diammonium hydrogen phosphate, a granular catalyst 5 (hereinafter referred to as the "granulated catalyst 5") was obtained in the same manner as that described in Catalyst preparation example 1. The Si/Al ratio within the granulated catalyst 5 was 200, the molar ratio between phosphorus and aluminum (P/Al ratio) was 0.23, and the amount of gallium (based on a value of 100% for the total mass of the crystalline aluminosilicate) was 0.2% by mass.

Catalyst Preparation Example 6

With the exception of impregnating 120 g of the proton-type crystalline aluminosilicate with 120 g of a 2.30% by mass aqueous solution of gallium nitrate octahydrate in order to support 0.4% by mass of gallium on the aluminosilicate (based on a value of 100% for the total mass of the crystalline aluminosilicate), a granular catalyst 6 (hereinafter referred to as the "granulated catalyst 6") was obtained in the same manner as that described in Catalyst preparation example 1. The Si/Al ratio within the granulated catalyst 6 was 15, the molar ratio between phosphorus and aluminum (P/Al ratio) was 0.23, and the amount of gallium (based on a value of 100% for the total mass of the crystalline aluminosilicate) was 0.4% by mass.

Catalyst Preparation Example 7

With the exception of impregnating 120 g of the proton-type crystalline aluminosilicate with 120 g of a 4.03% by mass aqueous solution of gallium nitrate octahydrate in order to support 0.7% by mass of gallium on the aluminosilicate (based on a value of 100% for the total mass of the crystalline aluminosilicate), a granular catalyst 7 (hereinafter referred to as the "granulated catalyst 7") was obtained in the same manner as that described in Catalyst preparation example 1. The Si/Al ratio within the granulated catalyst 7 was 15, the molar ratio between phosphorus and aluminum (P/Al ratio) was 0.23, and the amount of gallium (based on a value of 100% for the total mass of the crystalline aluminosilicate) was 0.7% by mass.

Catalyst Preparation Example 8

With the exception of impregnating 120 g of the proton-type crystalline aluminosilicate with 120 g of a 5.75% by mass aqueous solution of gallium nitrate octahydrate in order to support 1.0% by mass of gallium on the aluminosilicate (based on a value of 100% for the total mass of the crystalline aluminosilicate), a granular catalyst 8 (hereinafter referred to as the "granulated catalyst 8") was obtained in the same manner as that described in Catalyst preparation example 1. The Si/Al ratio within the granulated catalyst 8 was 15, the molar ratio between phosphorus and aluminum (P/Al ratio) was 0.23, and the amount of gallium (based on a value of 100% for the total mass of the crystalline aluminosilicate) was 1.0% by mass.

Catalyst Preparation Example 9

With the exception of impregnating 120 g of the proton-type crystalline aluminosilicate with 120 g of a 8.63% by mass aqueous solution of gallium nitrate octahydrate in order to support 1.5% by mass of gallium on the aluminosilicate (based on a value of 100% for the total mass of the crystalline aluminosilicate), a granular catalyst 9 (hereinafter referred to as the "granulated catalyst 9") was obtained in the same manner as that described in Catalyst preparation example 1. The Si/Al ratio within the granulated catalyst 9 was 15, the molar ratio between phosphorus and aluminum (P/Al ratio) was 0.23, and the amount of gallium (based on a value of 100% for the total mass of the crystalline aluminosilicate) was 1.5% by mass.

Catalyst Preparation Example 10

120 g of a proton-type crystalline aluminosilicate having an MFI structure and a silicon/aluminum molar ratio (Si/Al ratio) of 35 was impregnated with 120 g of a 1.15% by mass aqueous solution of gallium nitrate octahydrate in order to support 0.2% by mass of gallium on the aluminosilicate (based on a value of 100% for the total mass of the crystalline aluminosilicate), and the resulting product was then dried at 120° C. Subsequently, the product was calcined for 3 hours at 780° C. under a stream of air, yielding a gallium-supporting crystalline aluminosilicate.

Tablet molding was then performed by applying a pressure of 39.2 MPa (400 kgf) to the obtained catalyst, and the resulting tablets were subjected to coarse crushing and then classified using a 20 to 28 mesh size, thus yielding a granular catalyst 10 (hereinafter referred to as the "granulated catalyst 10"). The Si/Al ratio within the granulated catalyst 10 was 35, the molar ratio between phosphorus and aluminum (P/Al ratio) was 0, and the amount of gallium (based on a value of 100% for the total mass of the crystalline aluminosilicate) was 0.2% by mass.

Catalyst Preparation Example 11

120 g of a proton-type crystalline aluminosilicate having an MFI structure and a silicon/aluminum molar ratio (Si/Al ratio) of 35 was impregnated with 120 g of a 1.15% by mass aqueous solution of gallium nitrate octahydrate in order to support 0.2% by mass of gallium on the aluminosilicate (based on a value of 100% for the total mass of the crystalline aluminosilicate), and the resulting product was then dried at 120° C. Subsequently, the product was calcined for 3 hours at 780° C. under a stream of air, yielding a gallium-supporting crystalline aluminosilicate.

Subsequently, 30 g of the obtained gallium-supporting crystalline aluminosilicate was impregnated with 30 g of a 0.37% by mass aqueous solution of diammonium hydrogen phosphate, and the resulting product was then dried at 120° C. Subsequently, the product was calcined for 3 hours at 780° C. under a stream of air, yielding a catalyst containing the crystalline aluminosilicate, gallium and phosphorus.

Tablet molding was performed by applying a pressure of 39.2 MPa (400 kgf) to the obtained catalyst, and the resulting tablets were subjected to coarse crushing and then classified using a 20 to 28 mesh size, thus yielding a granular catalyst 11 (hereinafter referred to as the "granulated catalyst 11"). The Si/Al ratio within the granulated catalyst 11 was 35, the molar ratio between phosphorus and aluminum (P/Al ratio) was 0.06, and the amount of gallium (based on a value of 100% for the total mass of the crystalline aluminosilicate) was 0.2% by mass.

Catalyst Preparation Example 12

With the exception of impregnating the gallium-supporting crystalline aluminosilicate with 30 g of a 5.47% by mass aqueous solution of diammonium hydrogen phosphate, a granular catalyst 12 (hereinafter referred to as the "granulated catalyst 12") was obtained in the same manner as that described in Catalyst preparation example 11. The Si/Al ratio within the granulated catalyst 12 was 35, the molar ratio between phosphorus and aluminum (P/Al ratio) was 0.90, and the amount of gallium (based on a value of 100% for the total mass of the crystalline aluminosilicate) was 0.2% by mass.

Catalyst Preparation Example 13

With the exception of impregnating the gallium-supporting crystalline aluminosilicate with 30 g of a 7.30% by mass aqueous solution of diammonium hydrogen phosphate, a granular catalyst 13 (hereinafter referred to as the "granulated catalyst 13") was obtained in the same manner as that described in Catalyst preparation example 11. The Si/Al ratio within the granulated catalyst 13 was 35, the molar ratio between phosphorus and aluminum (P/Al ratio) was 1.20, and the amount of gallium (based on a value of 100% for the total mass of the crystalline aluminosilicate) was 0.2% by mass.

Catalyst Preparation Example 14

A mixed solution containing 106 g of sodium silicate (J Sodium Silicate No. 3, $SiO_2$: 28 to 30% by mass, Na: 9 to 10% by mass, remainder: water, manufactured by Nippon Chemical Industrial Co., Ltd.) and pure water was added dropwise to a dilute sulfuric acid solution to prepare a silica sol aqueous solution ($SiO_2$ concentration: 10.2%). Meanwhile, distilled water was added to 20.4 g of the catalyst prepared in Catalyst preparation example 6 containing a crystalline aluminosilicate, gallium and phosphorus to prepare a zeolite slurry. The zeolite slurry was mixed with 300 g of the silica sol aqueous solution, and the resulting slurry was spray dried at 250° C., yielding a spherically shaped catalyst. Subsequently, the catalyst was calcined for 3 hours at 600° C., yielding a powdered catalyst 1 (hereinafter referred to as the "powdered catalyst 1").

With respect to the crystalline aluminosilicate within the powdered catalyst 1 excluding the binder, the Si/Al ratio was 15, the molar ratio between phosphorus and aluminum (P/Al ratio) was 0.23, and the amount of gallium (based on a value of 100% for the total mass of the crystalline aluminosilicate) was 0.4% by mass.

Catalyst Preparation Example 15

With the exception of using the catalyst synthesized in Catalyst preparation example 8, containing a crystalline aluminosilicate, gallium and phosphorus, a powdered catalyst 2 (hereinafter referred to as the "powdered catalyst 2") was obtained in the same manner as that described in Catalyst preparation example 14.

With respect to the crystalline aluminosilicate within the powdered catalyst 1 excluding the binder, the Si/Al ratio was 15, the molar ratio between phosphorus and aluminum (P/Al ratio) was 0.23, and the amount of gallium (based on a value of 100% for the total mass of the crystalline aluminosilicate) was 1.0% by mass.

Catalyst Preparation Example 16

With the exception of using the catalyst synthesized in Catalyst preparation example 10, containing a crystalline aluminosilicate and gallium, a powdered catalyst 3 (hereinafter referred to as the "powdered catalyst 3") was obtained in the same manner as that described in Catalyst preparation example 14.

With respect to the crystalline aluminosilicate within the powdered catalyst 1 excluding the binder, the Si/Al ratio was 35, the molar ratio between phosphorus and aluminum (P/Al ratio) was 0.0, and the amount of gallium (based on a value of 100% for the total mass of the crystalline aluminosilicate) was 0.2% by mass.

Catalyst Preparation Example 17

With the exception of using the catalyst synthesized in Catalyst preparation example 2, containing a crystalline aluminosilicate, gallium and phosphorus, a powdered catalyst 4 (hereinafter referred to as the "powdered catalyst 4") was obtained in the same manner as that described in Catalyst preparation example 14.

With respect to the crystalline aluminosilicate within the powdered catalyst 1 excluding the binder, the Si/Al ratio was 35, the molar ratio between phosphorus and aluminum (P/Al ratio) was 0.23, and the amount of gallium (based on a value of 100% for the total mass of the crystalline aluminosilicate) was 0.2% by mass.

Catalyst Preparation Example 18

With the exception of using the catalyst synthesized in Catalyst preparation example 13, containing a crystalline aluminosilicate, gallium and phosphorus, a powdered catalyst 5 (hereinafter referred to as the "powdered catalyst 5") was obtained in the same manner as that described in Catalyst preparation example 14.

With respect to the crystalline aluminosilicate within the powdered catalyst 1 excluding the binder, the Si/Al ratio was 35, the molar ratio between phosphorus and aluminum (P/Al ratio) was 1.2, and the amount of gallium (based on a value of 100% for the total mass of the crystalline aluminosilicate) was 0.2% by mass.

Catalyst Preparation Example 19

With the exception of impregnating 120 g of the proton-type crystalline aluminosilicate having an MFI structure and a silicon/aluminum molar ratio (Si/Al ratio) of 15 with 120 g of a 0.91% by mass aqueous solution of zinc nitrate hexahydrate in order to support 0.2% by mass of zinc on the aluminosilicate (based on a value of 100% for the total mass of the crystalline aluminosilicate), a granular catalyst 14 (hereinafter referred to as the "granulated catalyst 14") was obtained in the same manner as that described in Catalyst preparation example 1. The Si/Al ratio within the granulated catalyst 14 was 15, the molar ratio between phosphorus and aluminum (P/Al ratio) was 0.23, and the amount of zinc (based on a value of 100% for the total mass of the crystalline aluminosilicate) was 0.2% by mass.

Catalyst Preparation Example 20

With the exception of impregnating 120 g of the proton-type crystalline aluminosilicate with 120 g of a 1.82% by mass aqueous solution of zinc nitrate hexahydrate in order to support 0.4% by mass of zinc on the aluminosilicate (based on a value of 100% for the total mass of the crystalline aluminosilicate), a granular catalyst 15 (hereinafter referred to as the "granulated catalyst 15") was obtained in the same manner as that described in Catalyst preparation example 6. The Si/Al ratio within the granulated catalyst 15 was 15, the molar ratio between phosphorus and aluminum (P/Al ratio) was 0.23, and the amount of zinc (based on a value of 100% for the total mass of the crystalline aluminosilicate) was 0.4% by mass.

Catalyst Preparation Example 21

With the exception of impregnating 120 g of the proton-type crystalline aluminosilicate with 120 g of a 3.19% by mass aqueous solution of zinc nitrate hexahydrate in order to support 0.7% by mass of zinc on the aluminosilicate (based on a value of 100% for the total mass of the crystalline aluminosilicate), a granular catalyst 16 (hereinafter referred to as the "granulated catalyst 16") was obtained in the same manner as that described in Catalyst preparation example 7. The Si/Al ratio within the granulated catalyst 16 was 15, the molar ratio between phosphorus and aluminum (P/Al ratio) was 0.23, and the amount of zinc (based on a value of 100% for the total mass of the crystalline aluminosilicate) was 0.7% by mass.

Catalyst Preparation Example 22

With the exception of impregnating 120 g of the proton-type crystalline aluminosilicate with 120 g of a 4.55% by mass aqueous solution of zinc nitrate hexahydrate in order to support 1.0% by mass of zinc on the aluminosilicate (based on a value of 100% for the total mass of the crystalline aluminosilicate), a granular catalyst 17 (hereinafter referred to as the "granulated catalyst 17") was obtained in the same manner as that described in Catalyst preparation example 8. The Si/Al ratio within the granulated catalyst 17 was 15, the molar ratio between phosphorus and aluminum (P/Al ratio) was 0.23, and the amount of zinc (based on a value of 100% for the total mass of the crystalline aluminosilicate) was 1.0% by mass.

Catalyst Preparation Example 23

With the exception of impregnating 120 g of the proton-type crystalline aluminosilicate with 120 g of a 6.83% by mass aqueous solution of zinc nitrate hexahydrate in order to support 1.5% by mass of zinc on the aluminosilicate (based on a value of 100% for the total mass of the crystalline aluminosilicate), a granular catalyst 18 (hereinafter referred to as the "granulated catalyst 18") was obtained in the same manner as that described in Catalyst preparation example 9. The Si/Al ratio within the granulated catalyst 18 was 15, the molar ratio between phosphorus and aluminum (P/Al ratio) was 0.23, and the amount of zinc (based on a value of 100% for the total mass of the crystalline aluminosilicate) was 1.5% by mass.

Catalyst Preparation Example 24

18 g of fumed silica was impregnated with 30 g of a 13.4% by mass aqueous solution of gallium nitrate octahydrate, and the resulting product was dried at 120° C. Subsequently, the product was calcined for 3 hours at 780° C. under a stream of air, yielding a gallium-supporting fumed silica.

18 g of this gallium-supporting fumed silica was impregnated with 50 g of a 30% by mass aqueous solution of diammonium hydrogen phosphate, and the resulting product was dried at 120° C. Subsequently, the product was calcined for 3 hours at 780° C. under a stream of air, yielding a fumed silica containing gallium (3.1% by mass) and phosphorus (16.4% by mass).

18 g of this fumed silica containing gallium and phosphorus was mixed with 12 g of the catalyst prepared in Catalyst preparation example 1, the thus obtained catalyst was subjected to tablet molding by applying a pressure of 39.2 MPa (400 kgf), and the resulting tablets were subjected to coarse crushing and then classified using a 20 to 28 mesh size, thus yielding a granular catalyst 19 (hereinafter referred to as the "granulated catalyst 19"). The Si/Al ratio of the crystalline aluminosilicate contained within the granulated catalyst 19 was 15, the molar ratio between phosphorus and aluminum (P/Al ratio) was 0.23, and the amount of gallium (based on a value of 100% for the total mass of the crystalline aluminosilicate) was 0.2% by mass. Further, the amount of supported gallium within the catalyst was 1.9% by mass, and the amount of supported phosphorus was 9.8% by mass.

<Evaluations>

[Measurement of Yield of Monocyclic Aromatic Hydrocarbons During Initial Reaction: Measurement 1]

The initial reaction catalytic activity of each of the obtained granulated catalysts 1 to 9 and 14 to 18 was evaluated using the method outlined below.

Using a flow-type reaction apparatus in which the reactor had been charged with the granulated catalyst (10 ml), a feedstock oil having the properties shown in Table 1 was brought into contact with the granulated catalyst and reacted under conditions including a reaction temperature of 550° C. and a reaction pressure of 0 MPaG. During the reaction, nitrogen was introduced as a diluent so that the contact time between the feedstock oil and the granulated catalyst was 7 seconds.

Reaction was continued under these conditions for 30 minutes to produce monocyclic aromatic hydrocarbons of 6 to 8 carbon number, and a compositional analysis of the products was performed using an FID gas chromatograph connected directly to the reaction apparatus in order to measure the yield of monocyclic aromatic hydrocarbons during the initial reaction. The measurement results obtained using the granulated catalysts 1 to 9 are shown in Table 2. The measurement results obtained using the granulated catalysts 14 to 18 are shown in Table 3.

TABLE 1

| | Feedstock properties | | | Analysis method |
|---|---|---|---|---|
| Density | (Measurement temperature: 15° C.) | g/cm³ | 0.906 | JIS K 2249 |

TABLE 1-continued

| | Feedstock properties | | | Analysis method |
|---|---|---|---|---|
| Kinematic viscosity | (Measurement temperature: 30° C.) | mm²/s | 3.640 | JIS K 2283 |
| Distillation characteristics | Initial boiling point | ° C. | 175.5 | JIS K 2254 |
| | 10 volume % distillation temperature | ° C. | 224.5 | |
| | 50 volume % distillation temperature | ° C. | 274.0 | |
| | 90 volume % distillation temperature | ° C. | 349.5 | |
| | End point temperature | ° C. | 376.0 | |
| Compositional analysis | Saturated content | volume % | 35 | JPI-5S-49 |
| | Olefin content | volume % | 8 | |
| | Total aromatic content | volume % | 57 | |
| | Monocyclic aromatic content | volume % | 23 | |
| | Bicyclic aromatic content | volume % | 25 | |
| | Tricyclic and higher aromatic content | volume % | 9 | |

[Measurement of Yield of Monocyclic Aromatic Hydrocarbons During Initial Reaction: Measurement 2]

The initial reaction catalytic activity of the obtained powdered catalysts 1 and 2 was evaluated using the method outlined below.

Using a flow-type reaction apparatus in which the reactor had been charged with the powdered catalyst (400 g), a feedstock oil having the properties shown in Table 1 was brought into contact with the powdered catalyst and reacted under conditions including a reaction temperature of 550° C. and a reaction pressure of 0.1 MPaG. For the reaction, the powdered catalyst was packed in a reaction tube with a diameter of 60 mm. During the reaction, nitrogen was introduced as a diluent so that the contact time between the feedstock oil and the powdered catalyst was 10 seconds.

Reaction was continued under these conditions for 10 minutes to produce monocyclic aromatic hydrocarbons of 6 to 8 carbon number, and the gaseous products, the liquid products and the coke deposited on the catalyst were collected. A compositional analysis of the gaseous products was performed using a micro-gas chromatograph and an FID gas chromatograph connected directly to the reaction apparatus. A compositional analysis of the liquid products was performed using the FID gas chromatograph. The amount of coke on the catalyst was calculated using a $CO_2$ meter connected directly to the reaction apparatus. On the basis of these compositional analyses, the yield of monocyclic aromatic hydrocarbons during the initial reaction was measured. The measurement results are shown in Table 4.

TABLE 2

| | Catalyst | Si/Al ratio | P/Al ratio | Amount of Ga *1 (% by mass) | Amount of P *2 (% by mass) | Amount of Ga *2 (% by mass) | Yield of monocyclic aromatic hydrocarbons (% by mass) |
|---|---|---|---|---|---|---|---|
| Example 1 | Granulated catalyst 1 | 15 | 0.23 | 0.2 | 0.7 | 0.2 | 33 |
| Example 2 | Granulated catalyst 2 | 35 | 0.23 | 0.2 | 0.30 | 0.2 | 35 |
| Example 3 | Granulated catalyst 3 | 50 | 0.23 | 0.2 | 0.2 | 0.2 | 35 |
| Example 4 | Granulated catalyst 4 | 100 | 0.23 | 0.2 | 0.1 | 0.2 | 28 |
| Comparative example 1 | Granulated catalyst 5 | 200 | 0.23 | 0.2 | 0.05 | 0.2 | 23 |
| Example 5 | Granulated catalyst 6 | 15 | 0.23 | 0.4 | 0.7 | 0.4 | 31 |
| Example 6 | Granulated catalyst 7 | 15 | 0.23 | 0.7 | 0.7 | 0.7 | 28 |
| Example 7 | Granulated catalyst 8 | 15 | 0.23 | 1.0 | 0.7 | 1.0 | 27 |
| Comparative example 2 | Granulated catalyst 9 | 15 | 0.23 | 1.5 | 0.7 | 1.5 | 23 |

*1: Amount of Ga based on a value of 100% for the total mass of the crystalline aluminosilicate
*2: Amount of P or Ga based on the total mass of the catalyst

TABLE 3

| | Catalyst | Si/Al ratio | P/Al ratio | Amount of Zn *1 (% by mass) | Amount of P *2 (% by mass) | Amount of Zn *2 (% by mass) | Yield of monocyclic aromatic hydrocarbons (% by mass) |
|---|---|---|---|---|---|---|---|
| Example 8 | Granulated catalyst 14 | 15 | 0.23 | 0.2 | 0.7 | 0.2 | 30 |
| Example 9 | Granulated catalyst 15 | 15 | 0.23 | 0.4 | 0.7 | 0.4 | 33 |
| Example 10 | Granulated catalyst 16 | 15 | 0.23 | 0.7 | 0.7 | 0.7 | 31 |
| Example 11 | Granulated catalyst 17 | 15 | 0.23 | 1.0 | 0.7 | 1.0 | 30 |
| Comparative example 3 | Granulated catalyst 18 | 15 | 0.23 | 1.5 | 0.7 | 1.5 | 24 |

*1: Amount of Zn based on a value of 100% for the total mass of the crystalline aluminosilicate
*2: Amount of P or Zn based on the total mass of the catalyst

TABLE 4

| | Catalyst | Si/Al ratio | P/Al ratio | Amount of Ga *1 (% by mass) | Amount of P *2 (% by mass) | Amount of Ga *2 (% by mass) | Yield of monocyclic aromatic hydrocarbons (% by mass) |
|---|---|---|---|---|---|---|---|
| Example 12 | Powdered catalyst 1 | 15 | 0.23 | 0.4 | 0.28 | 0.16 | 27 |
| Example 13 | Powdered catalyst 2 | 15 | 0.23 | 1.0 | 0.28 | 0.40 | 25 |

*1: Amount of Ga based on a value of 100% for the total mass of the crystalline aluminosilicate
*2: Amount of P or Ga based on the total mass of the catalyst

[Measurement of Yield of Monocyclic Aromatic Hydrocarbons Under Pseudo-Steady State Conditions: Measurement 3]

The obtained granulated catalysts 2, 10 to 13 and 19 and the powdered catalysts 3 to 5 were each subjected to a hydrothermal treatment under conditions including a treatment temperature of 650° C. and a treatment time of 6 hours under a 100% by mass steam atmosphere, thus effecting a simulated hydrothermal degradation that yielded pseudo-steady state granulated catalysts 2, 10 to 13 and 19 and pseudo-steady state powdered catalysts 3 to 5. By using these hydrothermally degraded catalysts, the yield of monocyclic aromatic hydrocarbons under a pseudo-steady state was able to be evaluated.

With the exception of using these pseudo-degraded catalysts instead of the granulated catalysts, the same process as that described for measurement 1 was used to react the feedstock oil and then perform a compositional analysis of the resulting products to measure the yield of the monocyclic aromatic hydrocarbons. The measurement results are shown in Table 5 and Table 7.

Further, with the exception of using the pseudo-degraded powdered catalysts instead of the powdered catalysts, the same process as that described for measurement 2 was used to react the feedstock oil and then perform a compositional analysis of the resulting products to measure the yield of the monocyclic aromatic hydrocarbons. The measurement results are shown in Table 6.

TABLE 5

| | Catalyst | Si/Al ratio | P/Al ratio | Amount of Ga *1 (% by mass) | Amount of P *2 (% by mass) | Amount of Ga *2 (% by mass) | Yield of monocyclic aromatic hydrocarbons under pseudo-steady state (% by mass) |
|---|---|---|---|---|---|---|---|
| Comparative example 4 | Granulated catalyst 10 | 35 | 0.00 | 0.2 | 0.0 | 0.2 | 12 |
| Example 14 | Granulated catalyst 11 | 35 | 0.06 | 0.2 | 0.1 | 0.2 | 25 |
| Example 15 | Granulated catalyst 2 | 35 | 0.23 | 0.2 | 0.3 | 0.2 | 31 |
| Example 16 | Granulated catalyst 12 | 35 | 0.90 | 0.2 | 1.2 | 0.2 | 27 |
| Comparative example 5 | Granulated catalyst 13 | 35 | 1.20 | 0.2 | 1.6 | 0.2 | 12 |

*1: Amount of Ga based on a value of 100% for the total mass of the crystalline aluminosilicate
*2: Amount of P or Ga based on the total mass of the catalyst

TABLE 6

| | Catalyst | Si/Al ratio | P/Al ratio | Amount of Ga *1 (% by mass) | Amount of P *2 (% by mass) | Amount of Ga *2 (% by mass) | Yield of monocyclic aromatic hydrocarbons under pseudo-steady state (% by mass) |
|---|---|---|---|---|---|---|---|
| Comparative example 6 | Pseudo-degraded powdered catalyst 3 | 35 | 0.00 | 0.2 | 0.00 | 0.08 | 11 |
| Example 17 | Pseudo-degraded powdered catalyst 4 | 35 | 0.23 | 0.2 | 0.28 | 0.08 | 30 |
| Comparative example 7 | Pseudo-degraded powdered catalyst 5 | 35 | 1.20 | 0.2 | 1.40 | 0.08 | 12 |

*1: Amount of Ga based on a value of 100% for the total mass of the crystalline aluminosilicate
*2: Amount of P or Ga based on the total mass of the catalyst

TABLE 7

| | Catalyst | Si/Al ratio | P/Al ratio | Amount of Ga *1 (% by mass) | Amount of P *2 (% by mass) | Amount of Ga *2 (% by mass) | Yield of monocyclic aromatic hydrocarbons under pseudo-steady state (% by mass) |
|---|---|---|---|---|---|---|---|
| Example 18 | Granulated catalyst 19 | 15 | 0.23 | 0.2 | 9.8 | 1.9 | 25 |

*1: Amount of Ga based on a value of 100% for the total mass of the crystalline aluminosilicate
*2: Amount of P or Ga based on the total mass of the catalyst

21

<Results>

It is evident that examples 1 to 4, which used the granulated catalysts 1 to 4 respectively in which the Si/Al ratio within the crystalline aluminosilicate was not more than 100, produced superior yields of monocyclic aromatic hydrocarbons than comparative example 1 which had a Si/Al ratio of 200.

Further, it is also evident that example 1 and examples 5 to 7, in which the amount of gallium was not more than 1.2% by mass, produced superior yields of monocyclic aromatic hydrocarbons than comparative example 2 in which the amount of gallium was 1.5% by mass.

Similarly, in those cases where zinc was included in the catalysts, it is evident that examples 8 to 11, in which the amount of zinc was not more than 1.2% by mass, produced superior yields of monocyclic aromatic hydrocarbons than comparative example 3 in which the amount of zinc was 1.5% by mass.

Even in the case of the powdered catalysts, it is clear that examples 12 and 13 produced superior yields of monocyclic aromatic hydrocarbons than comparative example 2.

Moreover, examples 14 to 16, which used the pseudo-steady state granulated catalysts 2, 11 and 12 (pseudo-degraded catalysts 2, 11 and 12) in which the P/Al ratio was within a range from 0.01 to 1.0, produced superior yields of monocyclic aromatic hydrocarbons under steady state conditions than both comparative example 4, which used the pseudo-steady state granulated catalyst 10 (pseudo-degraded catalyst 10) in which the P/Al ratio was 0.00, and comparative example 5, which used the pseudo-steady state granulated catalyst 13 (pseudo-degraded catalyst 13) in which the P/Al ratio was 1.20.

Furthermore, it is also evident that example 17, which used the pseudo-steady state powdered catalyst 4 (pseudo-degraded powdered catalyst 4), produced a superior yield of monocyclic aromatic hydrocarbons under steady state conditions than both comparative example 6, which used the pseudo-steady state powdered catalyst 3 (pseudo-degraded powdered catalyst 3) in which the P/Al ratio was 0.00, and comparative example 7, which used the pseudo-steady state powdered catalyst 5 (pseudo-degraded powdered catalyst 5) in which the P/Al ratio was 1.20.

In example 18, which used the granulated catalyst 19 containing an inorganic oxide within the catalyst (pseudo-degraded catalyst 19), an improved result was confirmed for the yield of monocyclic aromatic hydrocarbons under steady state conditions.

From the above results, it was clear that by using a granulated catalyst or powdered catalyst in which the Si/Al ratio within the crystalline aluminosilicate was not more than 100, the P/Al ratio was not less than 0.01 and not more than 1.0, and the amount of gallium was not more than 1.2% by mass, the yield of monocyclic aromatic hydrocarbons could be increased, both during the initial reaction and under pseudo-steady state conditions.

The invention claimed is:

1. A method for producing monocyclic aromatic hydrocarbons of 6 to 8 carbon number, the method comprising bringing a feedstock oil containing polycyclic aromatic hydrocarbons and having a 10 volume % distillation temperature of at least 140° C. and an end point temperature of not more than 400° C. into contact with a catalyst comprising a medium pore size zeolite, gallium and/or zinc, and phosphorus,
wherein
a molar ratio between silicon and aluminum (Si/Al ratio) in the medium pore size zeolite is not more than 100,
a molar ratio between phosphorus supported on the medium pore size zeolite and aluminum within the medium pore size zeolite (P/Al ratio) is not less than 0.01 and not more than 1.0, and
an amount of gallium and/or zinc is not more than 1.2% by mass based on the mass of the medium pore size zeolite.

2. A method for producing monocyclic aromatic hydrocarbons of 6 to 8 carbon number, the method comprising bringing a feedstock oil containing polycyclic aromatic hydrocarbons and having a 10 volume % distillation temperature of at least 140° C. and a 90 volume % distillation temperature of not more than 350° C. into contact with a catalyst comprising a medium pore size zeolite, gallium and/or zinc, and phosphorus,
wherein
a molar ratio between silicon and aluminum (Si/Al ratio) in the medium pore size zeolite is not more than 100,
a molar ratio between phosphorus supported on the medium pore size zeolite and aluminum within the medium pore size zeolite (P/Al ratio) is not less than 0.01 and not more than 1.0, and
an amount of gallium and/or zinc is not more than 1.2% by mass based on the mass of the medium pore size zeolite.

3. The method according to claim 1, wherein a cracked gas oil produced in a fluid catalytic cracking is used as the feedstock oil.

4. The method according to claim 1, wherein the feedstock oil is brought into contact with the catalyst in a fluidized bed reactor.

5. The method according to claim 1, wherein an amount of phosphorus is within a range from 0.1 to 10% by mass based on the total mass of the catalyst, and an amount of gallium and/or zinc contained within the catalyst is not more than 2% by mass based on the total mass of the catalyst.

6. The method according to claim 1, wherein the medium pore size zeolite is a pentasil-type zeolite.

7. The method according to claim 1, wherein the medium pore size zeolite is an MFI-type zeolite.

8. The method according to claim 1, wherein a molar ratio between phosphorus supported on the medium pore size zeolite and aluminum within the medium pore size zeolite (P/Al ratio) is not more than 0.5.

9. The method according to claim 1, wherein an amount of gallium and/or zinc is not more than 1.0% by mass based on a mass of the medium pore size zeolite.

10. The method according to claim 2, wherein a cracked gas oil produced in a fluid catalytic cracking is used as the feedstock oil.

11. The method according to claim 2, wherein the feedstock oil is brought into contact with the catalyst in a fluidized bed reactor.

12. The method according to claim 2, wherein an amount of phosphorus is within a range from 0.1 to 10% by mass based on the total mass of the catalyst, and an amount of gallium and/or zinc contained within the catalyst is not more than 2% by mass based on the total mass of the catalyst.

13. The method according to claim 2, wherein the medium pore size zeolite is a pentasil-type zeolite.

14. The method according to claim 2, wherein the medium pore size zeolite is an MFI-type zeolite.

15. The method according to claim 2, wherein a molar ratio between phosphorus supported on the medium pore size zeolite and aluminum within the medium pore size zeolite (P/Al ratio) is not more than 0.5.

16. The method according to claim 2, wherein an amount of gallium and/or zinc is not more than 1.0% by mass based on a mass of the medium pore size zeolite.

\* \* \* \* \*